United States Patent
Conwell

(10) Patent No.: US 7,560,699 B2
(45) Date of Patent: Jul. 14, 2009

(54) SMALL FIELD-OF-VIEW DETECTOR HEAD ("SPECT") ATTENUATION CORRECTION SYSTEM

(75) Inventor: Richard L. Conwell, Del Mar, CA (US)

(73) Assignee: Digirad Corporation, Poway, CA (US)

( * ) Notice: Subject to any disclaimer, the term of this patent is extended or adjusted under 35 U.S.C. 154(b) by 37 days.

(21) Appl. No.: 11/067,293

(22) Filed: Feb. 25, 2005

(65) Prior Publication Data

US 2005/0189494 A1 Sep. 1, 2005

Related U.S. Application Data

(60) Provisional application No. 60/613,782, filed on Sep. 27, 2004, provisional application No. 60/548,071, filed on Feb. 25, 2004.

(51) Int. Cl.
*G01T 1/166* (2006.01)
(52) U.S. Cl. .................................. 250/363.04
(58) Field of Classification Search ............. 250/363.04
See application file for complete search history.

(56) References Cited

U.S. PATENT DOCUMENTS

| 4,580,219 | A | * | 4/1986 | Pelc et al. .................... 382/131 |
| 5,900,636 | A | * | 5/1999 | Nellemann et al. ...... 250/363.04 |
| 6,194,726 | B1 | | 2/2001 | Pi et al. |
| 6,201,247 | B1 | * | 3/2001 | Lutheran et al. ........ 250/363.04 |
| 6,324,242 | B1 | | 11/2001 | Pan |
| 2002/0079456 | A1 | | 6/2002 | Lingren et al. |
| 2002/0188197 | A1 | * | 12/2002 | Bishop et al. ............... 600/436 |

FOREIGN PATENT DOCUMENTS

WO   WO 00/13041         3/2000
WO   WO 03081220 A2 * 10/2003

* cited by examiner

*Primary Examiner*—David P Porta
*Assistant Examiner*—Shun Lee
(74) *Attorney, Agent, or Firm*—Law Ofc Scott Harris Inc

(57) ABSTRACT

A detector head having a small field of view, for example one which receives information from less than half a body imaged, is used to form a transmission attenuation map. The same detector head both receives information for the transmission attenuation map and also receives imaging information e.g. from a radioisotope.

15 Claims, 2 Drawing Sheets

SMALL FIELD-OF-VIEW DETECTOR HEAD ("SPECT") ATTENUATION CORRECTION SYSTEM

CROSS REFERENCE TO RELATED APPLICATIONS

The invention claims priority under 35 U.S.C. §119 to provisional application Ser. No. 60/548,071 filed Feb. 25, 2004 and Ser. No. 60/613,782 filed Sep. 27, 2004, the disclosures of which are incorporated herein by reference.

BACKGROUND

Single Photon Emission Computed Tomography imaging, also called "SPECT", attempts to produce a three-dimensional reconstruction of the intensity of the three-dimensional distribution of a photon-emitting element within the body of the subject being imaged. Typically the emitted photons are gamma rays emitted from a radiopharmaceutical. SPECT systems generate such three-dimensional reconstructions by applying one of several known computerized reconstruction techniques to multiple projection images acquired around the subject. Exemplary techniques include filtered back-projection, ordered subset expectation maximization (OSEM) and other iterative techniques.

Photons are emitted into the region outside the subject being imaged during SPECT. These photons are referred to herein as "external photons".

The mass of the subject attenuates the photons emitted within the subject ("internal photons"). Since the external photons are internal photons not lost to attenuation within the subject, the external photon intensity may vary from projection-to-projection.

If the attenuation properties of the mass along the path of each internal photon are known, a tomographic reconstruction technique can use this information to correct projection images for attenuation of the internal photons. This procedure is called attenuation correction.

Transmission computed tomography ("CT") can be used to determine the attenuation properties along any internal photon's path within the subject. CT typically employs x-ray or gamma ray photons to produce essentially an attenuation map of the mass of the subject within the volume being imaged. A transmission attenuation correction map can be produced in this way.

Conventional large Field-of-View Anger style gamma cameras equipped with transmission attenuation correction often use the emission detectors as transmitted photon detectors. The photon source for transmission attention correction is often one or more isotopic gamma ray sources. The logic used to determine the location and energy of photons impinging on the external photon detectors in Anger cameras may limit the maximum count rate of the system, resulting in density maps with relatively poor precision. The FOV of these detectors may be as wide as 50 cm. This may enable collection of the transmission projection with little or no truncation. Truncation occurs when some portion of the volume being measured is not completely sampled in the projections.

Other approaches to transmission attention correction are known.

DETAILED DESCRIPTION

Figure 1:
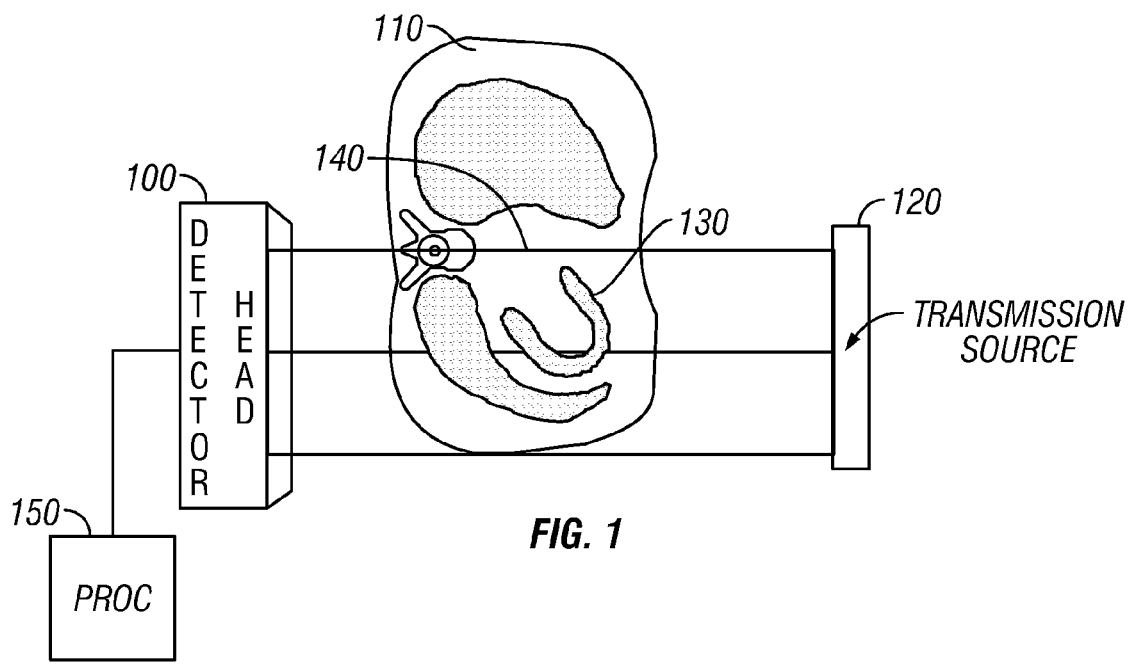
FIG. 1 illustrates an embodiment using a small field of view detector head with a parallel collimator and a planar or moving line source of transmission photons.

In dedicated cardiac SPECT imaging systems (such as upright rotating chair SPECT), the width of the FOV of the external photon detector(s) is typically smaller than the width of the subject in whom some region of interest (e.g., the heart) is to be imaged. As a result, it has been difficult to acquire a transmission attenuation map throughout the entire volume traversed by internal photons along their path to the external photon detector using a single small field of view detector.

Using an incomplete (truncated) attenuation map may lead to artifacts in the attenuation corrected SPECT image. Such artifacts may increase the probability of incorrect diagnosis.

An embodiment describes a medical imaging device, e.g. a Single Photon Emission Computed Tomography (SPECT) camera with one or more small field of view photon detector heads, to produce photon-emitting element density images corrected for attenuation of the internal photons by the mass distribution within the body of the subject. In the embodiment, each detector head covers less than the entire width of the object being imaged. No one head scans the entire body at any one time.

The embodiments may use a multi-crystal small field of view gamma camera detector head, a conventional Anger style gamma camera detector head or a small field of view solid-state detector head using CZT or a similar direct conversion semiconductor material.

In an embodiment, the detector head 100 need only be approximately as wide as one half the width of the subject 110 at the plane of the attenuation map to be measured, e.g., cover less than 50% of the area, less than 60% of the area, or less than 75% of the area. The embodiment describes this as a half-width detector.

This embodiment enables a computed tomographic image to be reconstructed from data collected using a half-width detector 100. The detector 100 is positioned so that one edge of the axial FOV is aligned with the axis of rotation. The subject is rotated, e.g. by 360° relative to the head. This enables sampling the entire area of the plane to be measured.

The information from the detector head 100 is sent to a processor 150 that determines the transmission attenuation information, and also obtains information related to the emission signal from the radioisotope.

An orienting part moves either the patient or the head. In the embodiment, the movement is relative to the axis 140 EGA rotation around the axis. The movement may be a movement of the body 110 around the axis. Alternatively, the movement may be a rotation of the detector head and/or transmission source around that axis.

At each of a plurality of different positions, for example each of a plurality of rotated positions, the transmission attenuation information is collected. A view of the entire object from all directions can therefore be obtained using a half width detector head.

Computation of the attenuation map in this embodiment may be performed using the Fast Fourier Back Projection method, abbreviated FFBP. Another computational technique employs the so called "potato peeler" perspective or variable sinogram method described articles by E. Y. Sidky and X. Pan, including "Mathematical Formulation of the Potato Peeler Prospective," IEEE 2002, in one or more patents, including Pan, U.S. Pat. No. 6,324,242, entitled Fast Reconstruction with Uniform Noise Properties in Half-Scan Tomography. Other computational approaches such as filtered back projection and OSEM may be applicable to the required image optimization.

FIG. 1 illustrates detector head 100 illustrated to have a parallel collimator 150. The transmission source 120 may be either a collimated planar source or a line source that travels across the field of view of the detector head 100, e.g., a gamma camera. The subject 110 is also shown with objects of interest 130, along axis of rotation 140.

Figure 2:
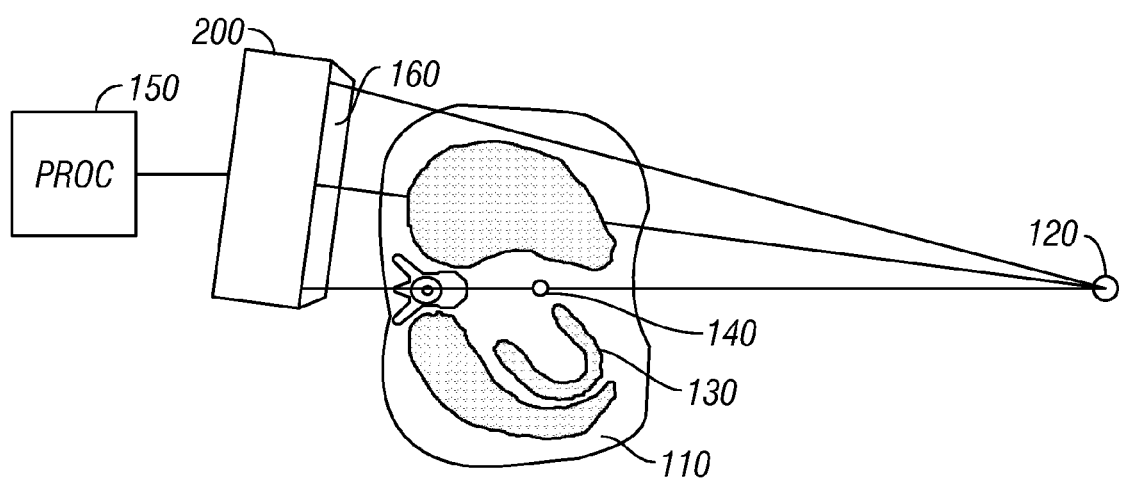
FIG. 2 depicts a second embodiment using a small field of view detector head with fan beam collimator and a line source or moving point source.

In other embodiments, the collimator 150 can be either a fan beam or half fan beam type, e.g., line focus collimators that transmit incident photons diverging in the horizontal plane, but parallel in the vertical plane. The transmission source 120 can be either a line source (collimated or uncollimated) positioned at the detector collimator's focal line or a collimated point source that travels along the focal line of the detector collimator. FIG. 2 illustrates the second embodiment using a fan beam collimator 160 as part of detector 200.

In both the configurations of FIG. 1 and FIG. 2 the detectors are illustrated in positions for half-width transmission attention correction. For SPECT, the same small field of view—detectors 100 would typically be positioned (or the subject positioned, or a combination of both) so that the organ of interest 130 will be centered on or near the axis of rotation 140, thereby allowing the organ of interest 130 to stay within the field of view during multiple emission projection acquisitions.

Figure 3:
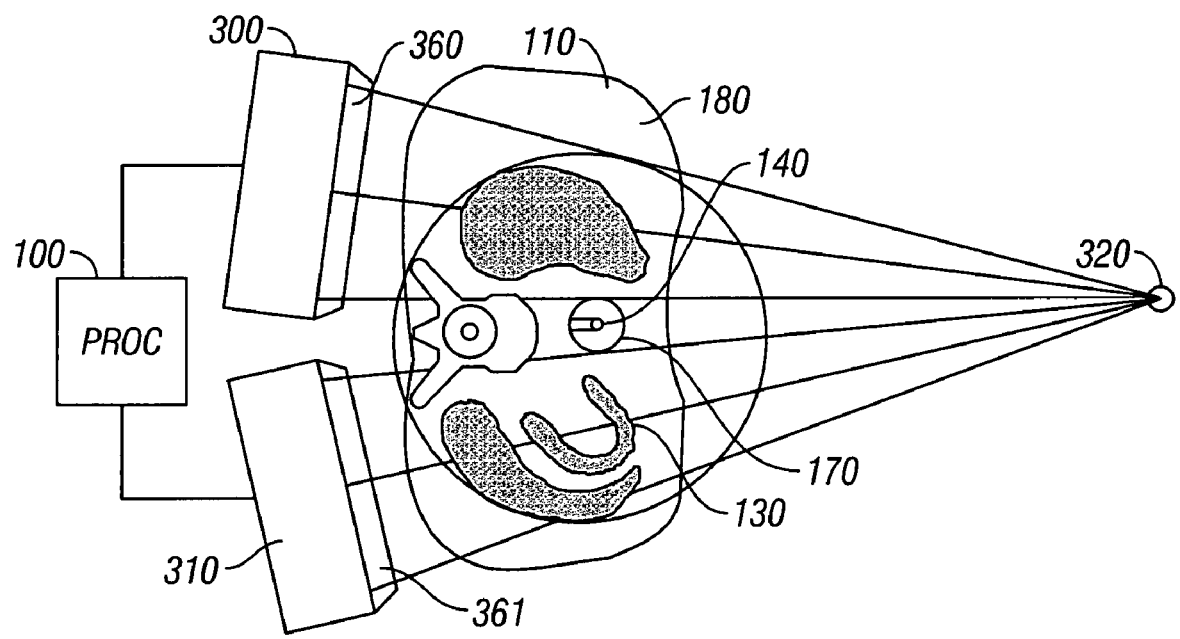
FIG. 3 illustrates a third embodiment, using two small field of view detector heads with fan beam collimators and a line source or moving point source.

In a third embodiment, two or more small field of view detectors 300, 310 with fan beam collimators 360, 361 are positioned together to form a substantially continuous transmitted photon, transmission attention correction detector whose combined width spans or substantially spans the width of the subject 110 whose transmission attention correction acquisition will be performed. FIG. 3 illustrates the arrangement of two such detector heads 300 and 310. The heads 300, 310 and transmission source 320 may rotate around the subject 110, or the subject 110 may rotate in front of the detectors 300, 310 and source 120.

FIG. 3 shows how the focal lines of the fan beam collimators 360, 361 attached to the detectors 300, 310 are positioned to focus on transmission source 320. This source may be either a line source (collimated or uncollimated) or a collimated point source that travels along the focal lines of the detector collimators 360,361. Placing the transmission source 320 in such a position increases the efficiency of the collimator to the activity of the transmission source while maintaining the same efficiency for any diffuse activity emanating from the subject as a result of the radiopharmaceutical injected to enable collection of the SPECT image. Accordingly, the positioning of the collimators 360, 361 and the transmission source 320 improves the signaltonoise ratio (SNR) of the transmission source 120 relative to the injected dose.

FIG. 3 also illustrates that various regions of the subject 110 undergoing transmission attention correction imaging may not be sampled, including an inner unsampled region 170 and an outer unsampled region 180. The size of the inner unsampled region 170 is a function of the space between the multiple detectors 300, 310 and the number of heads. FIG. 3 illustrates that how a two head embodiment will form a disk shaped inner region 170. If three or more heads are used, the inner region 170 will be a ring. Increasing the separation between the heads 100 correspondingly increases the volume of the inner unsampled region 170 but reduces the volume of the outer unsampled region 180. However, the outer unsampled volume 180 decreases much faster than the inner unsampled volume increases.

One embodiment increases the inner unsampled volume to take benefit of a larger reduction of the outer unsampled volume. Smaller unsampled (truncated) volumes will typically be associated with more accurate attenuation maps. The concept of not sampling some of the inner region so as to maximize the sampling of the outer region is an important feature of this disclosure. The line defining the edge of the outer unsampled volume 180 should point to the region outside the lungs as shown.

Figure 4:
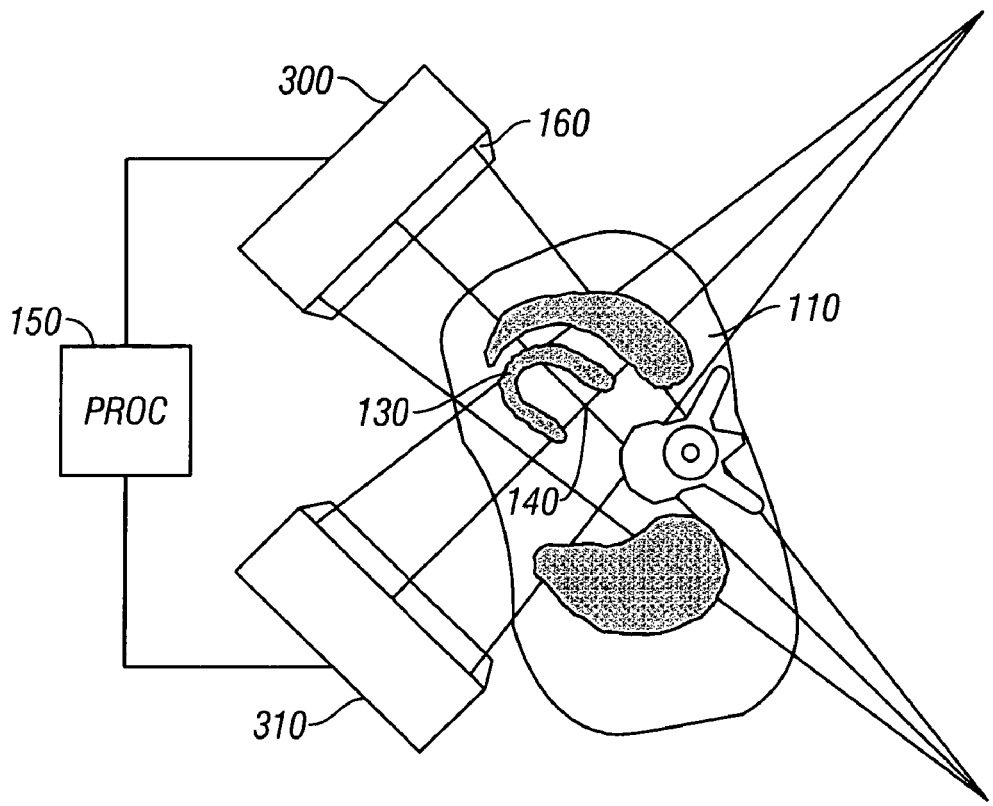
FIG. 4 depicts an embodiment with two small field of view detector heads with fan beam collimators and a line source or moving point source.

FIG. 4 illustrates how these same small field of view detectors 300, 310 would be repositioned for SPECT imaging the organ of interest 130.

The small field of view detector heads 100 may be equipped with either a conventional single or multi-crystal scintillator. In such heads, the photodetectors are typically arrays of photodiodes constructed in semiconductor materials such as silicon—Si—or conventional or position sensitive photomultiplier tubes—PMTs or PSPMTs, respectively. These photodetectors are not capable of direct external photon—to electron conversion. Instead, they detect ultraviolet, visible or near infrared photons emitted from the scintillator crystals in response to detection of an external photon.

Alternatively, the photodetectors of the small field of view detector heads may be arrays of wide bandgap, direct detection semiconductors such as cadmium zinc telluride—CZT—that are capable of direct gamma-ray photon-to-electron conversion. Such materials may have a higher gamma-ray photon-to-electron conversion efficiency than a scintillator-photodiode configuration.

Camera heads using multi-crystal scintillators and arrays of conventional semiconductor photodiodes, PMTs or one or more PSPMTS; or arrays of direct conversion semiconductor elements are called multiple detection element detectors. The independence of the detection elements of multi-element detectors may enable higher detection rates without pulse pile-up or paralysis. An embodiment may use one or more multi-crystal scintillators, conventional photodiodes, PMTs or PSPMTs, or head(s) equipped with an array of direct conversion semiconductor detector elements for both transmission attention correction and SPECT acquisition.

Another embodiment uses a modification of the "sparse readout" method disclosed in Lingren et al., U.S. Pat. No. 5,847,396, entitled Semiconductor Gamma-Ray Camera and Medical Imaging System to improve, perhaps significantly, the counting rate of a multi-element detector head(s). Such a readout system recognizes a detection element as having detected a valid signal suitable for processing when the magnitude of the signal detected in that element during a given readout cycle exceeds a preset level. In response, a flag is set, directing the readout system to "read" the signal magnitude associated with the flagged element during that readout cycle, enabling the image processing system to include the valid signal in the data to be processed. The sparse readout approach works well for detection systems where the data rate is low, e.g., the typical situation in nuclear medicine SPECT imaging. As noted earlier, however, placing the transmission attention correction transmission source 120 at the focal line of a fan beam collimator 160 increases the efficiency of the detector 100 for the transmission attention correction photon source. This may result in counting rates high enough to saturate a sparse readout system.

The sparse readout may be operated in two distinct modes to resolve such count rate issues. A first normal operating mode has been described above.

A second mode operates by manipulating the preset threshold level for flag setting to an optimal value for the detection of the photons emitted by the transmission source. The system identifies detection of a valid transmission photon by a particular detection element by the presence of a flag at the corresponding location. In this mode, the readout system counts only flags set for detection elements that have detected a transmission photon. The system ignores any additional information, such as the photon energy of the detected signal. Counting only flags may decrease the total data rate and therefore may significantly increase the maximum count rate capability of the readout system.

The mode of operation of the readout system may be determined by whether SPECT data or transmission data are being collected. The preset level may be set to reject Compton scattering of photons emitted by the transmission source 120. Additionally, if the transmission source photon energy is higher than that of the emission source photons used for the SPECT imaging, the readout may reject all photons emitted by the SPECT source (radiopharmaceutical).

The second readout mode for transmission attention correction is applicable to physical configurations and image processing methods of the embodiments described and as depicted in FIGS. 1 through 4.

Although cardiac SPECT imaging of a human is one application of the configurations described herein, these and additional novel configurations, signal collection and signal processing may be used to acquire transmission data to enable transmission attention correction on any nuclear image acquired from a human, an animal, or other subject. In addition, the embodiments disclosed and other embodiments according to this disclosure may be used with camera heads not considered small field of view. Furthermore, although this document uses an isotopic transmission source as an example, a suitably selected x-ray tube or other radiation source may be used as a source of transmission photons.

Although only a few embodiments have been disclosed in detail above, other modifications are possible, and this disclosure is intended to cover all such modifications, and most particularly, any modification which might be predictable to a person having ordinary skill in the art. For example, while the above has described determining the attenuation map using CT and obtaining the actual imaging using radiopharmaceuticals, it should be understood that other forms can be used. An important feature is that same detector head receive both the information for the attenuation map and the actual SPECT organ(s) scan, in order to avoid resolution reduction by patient movement. Also, cone beam collimators and point sources could be substituted for and used in place of the other collimators and sources described above.

Also, only those claims which use the words "means for" are intended to be interpreted under 35 USC 112, sixth paragraph. Moreover, no limitations from the specification are intended to be read into any claims, unless those limitations are expressly included in the claims.

What is claimed is:

1. A system for detecting emissions from an object within a body comprising:
    a transmission source, which produces an output transmission along a line through the body;
    a first detector head, which detects information from the transmission source, and also detects a emission signal from the object, said first detector head being sized to detect said transmission information from a maximum portion of 60% or less of said body at any given time, said first detector head oriented to detect information from an area defining its imaging area, and wherein said first detector head is oriented such that said area has a center and said center of said area is spaced from a central portion of said body;
    an orienting part which orients said body relative to the transmission source and detector head in a plurality of different orientations by rotating one of said body or said transmission source around said central portion of said body using said central portion of said body as an axis of rotation, and such that a center most portion of said imaging area of said first detector head is offset from said axis of rotation; and
    a processor, that forms a transmission attenuation correction map from said output transmission, and uses said transmission attenuation map to correct the information received from said emission signal, said first detector head and said processor producing output information indicative of less than all of said body, after said plurality of orientations of said orienting part, where said processor computes said transmission attenuation correction map of said body that is centered at said central portion.

2. A system as in claim 1, wherein said first detector head is a half width detector head which detects said transmission information from 50% or less of said body, at any given time, and orienting part rotates said body to at least one first position where only one part of said body only on one side of said central portion is being imaged, and wherein in said first position, only information from said half of said body on one side of said central portion is received, wherein said orienting part rotates said body around said central portion, using said central portion of said body to be imaged as an axis of rotation.

3. A system as in claim 1, wherein said transmission source transmits collimated beams.

4. A system as in claim 1, wherein said transmission source transmits fan shaped beams along a plane perpendicular to the axis of rotation of the system but parallel beams parallel to said axis.

5. A system as in claim 1, wherein said orienting part rotates said body around said central portion, using said central portion of said body to be imaged as said axis of rotation.

6. A system as in claim 1, wherein said orienting part moves at least one of the transmission source and detector head.

7. A system as in claim 1 wherein said orienting part rotates relative to an axis of rotation which is close to said object.

8. A system as in claim 1, further comprising a second detector head, separated from said first detector head, said first and second detector heads collectively covering detects said transmission information from 60% or less of said body at any given time.

9. A method comprising:
    receiving first image information in a detector head that covers a maximum of 60% or less of a total body to be imaged at any given time, said detector head oriented to detect information from an imaging area, and wherein a central portion of said imaging area is offset from a central portion of said body to be imaged;
    using said first image information to form a transmission attenuation map;
    receiving second image information in the detector head, from a different source than said first image information by changing an orientation between said detector head and said body to a plurality of different orientations by rotating one of said body and detector head around said central portion of said body using said central portion of said body to be imaged as an axis of rotation;

wherein a center portion of said detector head is offset from said central portion of said body; and using said transmission attenuation map of said first image information to correct an image obtained from said second information, and to obtain medical imaging information about at least one object within the body, said medical imaging information representing information about all of said plurality of different orientations, and representing less than all of said body.

10. A method as in claim 9, wherein said detector head receives and collimates parallel beams.

11. A method as in claim 9, wherein said detector head receives a collimated fan shape beam that is oriented perpendicular to the axis of rotation.

12. A method as in claim 9, wherein said detector head is formed of two separated detector heads.

13. A method as in claim 9, wherein said changing an orientation comprises rotating the object to be imaged around said axis of rotation relative to the detector head and where that axis of rotation is offset from a central portion of the imaging area.

14. A method as in claim 13, wherein said rotating rotates said body to at least one first position where only half of said body on one side of said central portion is being imaged, and wherein in said first position, only information from said half of said body on one side of said central portion is received.

15. A method as in claim 9, wherein said changing an orientation comprises rotating the detector head relative to the object to be imaged.

\* \* \* \* \*